US011642371B2

(12) United States Patent
Seto et al.

(10) Patent No.: US 11,642,371 B2
(45) Date of Patent: May 9, 2023

(54) ENCAPSULATED ANTIMICROBIALS AND RELATED METHODS OF TREATMENT

(71) Applicant: ADVANTAGE SILVER DENTAL ARREST, LLC, Salem, OR (US)

(72) Inventors: Jong Seto, San Francisco, CA (US); Peter M. Milgrom, Seattle, WA (US)

(73) Assignee: ADVANTAGE SILVER DENTAL ARREST, LLC, Salem, OR (US)

( * ) Notice: Subject to any disclaimer, the term of this patent is extended or adjusted under 35 U.S.C. 154(b) by 22 days.

(21) Appl. No.: 17/108,947

(22) Filed: Dec. 1, 2020

(65) Prior Publication Data

US 2021/0145758 A1    May 20, 2021

Related U.S. Application Data

(63) Continuation of application No. PCT/US2019/026017, filed on Apr. 5, 2019.

(60) Provisional application No. 62/688,149, filed on Jun. 21, 2018.

(51) Int. Cl.
| | | |
|---|---|---|
| A61K 9/50 | (2006.01) | |
| A61K 33/38 | (2006.01) | |
| A61P 1/02 | (2006.01) | |
| A61K 9/00 | (2006.01) | |
| A61K 47/02 | (2006.01) | |
| A61K 47/16 | (2006.01) | |
| A61K 47/32 | (2006.01) | |
| A61K 47/34 | (2017.01) | |
| A61K 47/46 | (2006.01) | |
| A61K 45/06 | (2006.01) | |

(52) U.S. Cl.
CPC ............ *A61K 33/38* (2013.01); *A61K 9/0053* (2013.01); *A61K 9/501* (2013.01); *A61K 9/5073* (2013.01); *A61K 9/5089* (2013.01); *A61K 45/06* (2013.01); *A61K 47/02* (2013.01); *A61K 47/16* (2013.01); *A61K 47/32* (2013.01); *A61K 47/34* (2013.01); *A61K 47/46* (2013.01); *A61P 1/02* (2018.01)

(58) Field of Classification Search
CPC ......... A61P 1/02; A61K 33/38; A61K 9/0053; A61K 9/501; A61K 9/5073; A61K 47/02; A61K 47/16; A61K 47/32; A61K 47/34; A61K 47/46; A61K 9/5089; A61K 45/06
See application file for complete search history.

(56) References Cited

U.S. PATENT DOCUMENTS

| | | |
|---|---|---|
| 6,007,795 A | 12/1999 | Masterman et al. |
| 8,808,718 B2 | 8/2014 | Van Der Waal et al. |
| 2002/0064541 A1 | 5/2002 | Lapidot et al. |
| 2006/0246149 A1 | 11/2006 | Buchholz et al. |
| 2009/0191279 A1 | 7/2009 | Kennard et al. |
| 2013/0017238 A1 | 1/2013 | Porter et al. |
| 2015/0216765 A1 | 8/2015 | Le Quay et al. |
| 2016/0251571 A1 | 9/2016 | Agrawal et al. |

FOREIGN PATENT DOCUMENTS

| | | | | |
|---|---|---|---|---|
| CN | 101355922 | * | 1/2009 | |
| CN | 104826114 | * | 8/2015 | |
| CN | 104826114 A | | 8/2015 | |
| JP | H09-110463 A | | 4/1997 | |
| WO | 2012119155 A1 | | 9/2012 | |
| WO | WO-2012119155 A1 * | | 9/2012 | ............ A01N 47/44 |
| WO | WO-2015035475 A1 * | | 3/2015 | ............ A01N 25/28 |
| WO | 2015074028 A1 | | 5/2015 | |

OTHER PUBLICATIONS

Rosenblatt, et al, Silver Diamine Fluoride: A Caries "Silver-Fluoride Bullet", 88 J Dent. Res. 116 (Year: 2009).*
CN101355922 Machine Translation (Year: 2009).*
Non-Final Office Action for corresponding U.S. Appl. No. 17/252,963; dated Jun. 17, 2022 (20 pages).
Examination Report for corresponding British application No. GB2100728.1; dated Mar. 14, 2022 (7 pages).
Fullriede, Hendrik, et al. "pH-responsive release of chlorhexidine from modified nanoporous silica nanoparticles for dental applications." BioNanoMaterials 17.1-2 (2016): 59-72.
Fluoride Varnish and Silver Diamine Fluoride: Fluoride Release Analysis and Clinical Guidance, American Dental Association, ADA Professional Product Review, Nov. 9, 2017, pp. 1-7, vol. 12, issue 2.
Carounanidy et al., Dental caries: A Complete Changeover, Part III: Changeover in the Treatment Decisions and Treatments, Journal of Conservative Dentistry, 2010, pp. 209-217, vol. 13, issue 4.
Chu et al., Uses of Sodium Fluoride Varnish in Dental Practice, Annals of the Royal Australasian College of Dental Surgeons, 2008, pp. 58-61, vol. 19.
Donovan et al., Annual Review of Selected Scientific Literature: Report of the Committee on Scientific Investigation of the American Academy of Restorative Dentistry, the Journal of Prosthetic Dentistry, 2017, pp. 281-346, vol. 118, issue 3.
Kianoush et al., Bacterial Profile of Dentine Caries and the Impact of pH on Bacterial Population Diversity, Plos One, 2014, pp. 1-10, vol. 9, issue 3, e92940.
International Application No. PCT/US2019/026017, International Search Report and Written Opinion dated Jul. 18, 2019, 9 pages.
Rosenblatt et al., Silver Diamine Fluoride: A Caries Silver-Fluoride Bullet, Journal of Dental Research, 2009, pp. 116-125, vol. 88, issue 2.
Suliga et al., Analysis of Atomic Oxygen and Ultraviolet Exposure Effects on Cycloaliphatic Epoxy Resins Reinforced with Octa-Functional POSS, Acta Astronautica, 2017, pp. 1-22, vol. 142.

(Continued)

*Primary Examiner* — Sean M Basquill
(74) *Attorney, Agent, or Firm* — Mendelsohn Dunleavy, P.C.; Garth M. Dahlen (57) ABSTRACT

The invention provides compositions and methods that comprise encapsulated silver diamine fluoride or other antimicrobial materials for use in treatment of dental caries, for example.

10 Claims, 6 Drawing Sheets

(56) References Cited

OTHER PUBLICATIONS

Examination Report for corresponding British application No. GB2100728.1; dated Sep. 12, 2022 (4 pages).
Non-Final Office Action for U.S. Appl. No. 17/252,963, dated Feb. 28, 2023 (16 pages).
Final Office Action for U.S. Appl. No. 17/252,963, dated Nov. 21, 2022 (14 pages).

* cited by examiner

ENCAPSULATED ANTIMICROBIALS AND RELATED METHODS OF TREATMENT

CROSS-REFERENCE TO RELATED APPLICATIONS

This application is a bypass continuation of International Application No. PCT/US2019/026017, filed Apr. 5, 2019, which claims priority to U.S. Provisional Application No. 62/688,149, filed Jun. 21, 2018, each of which is hereby incorporated herein by reference in its entirety.

GOVERNMENT LICENSE RIGHTS

This invention was made with government support under National Institute of Health (NIH) Small Business Innovation Research grants 1R43 DE022986 and No. 2 R44 DE022986 awarded by NIH. The government has certain rights in the invention.

BACKGROUND OF THE INVENTION

Dental caries is a bacterial infection whose metabolic acid byproducts etch, decalcify, and ultimately cause tooth cavitation, or dental decay. Untreated dental caries are a significant public health problem. One in every seven U.S. children ages 2 to 8 years has untreated dental caries in primary teeth (Dye et al., NCHS data brief, no 191. Hyattsville, Md., National Center for Health Statistics, 2015).

The application of a fluoride varnish is a well-established primary intervention for preventing dental caries. However, such treatment does not restore deeper cavitated lesions. Untreated dental decay extending through the tooth's enamel layer requires mechanical removal of decayed tissue with hand instruments or powered dental drills. Tooth structure lost during removal of the decayed lesion is restored with dental fillings or full coverage crowns.

Non-invasive, interim interventions for arresting untreated dental caries have been needed, especially in underserved populations lacking timely access to restorative dental services.

Silver diamine fluoride (SDF) received U.S. Food and Drug Administration approval in 2014 as a device for treating dental hypersensitivity. SDF is an inexpensive, non-invasive medicament that is applied topically as 38% SDF, a silver fluoride salt made soluble in water through the addition of ammonia. SDF has not been approved as a medicament for arresting dental caries; it is administered in children and adults for this purpose as an off-label use. SDF has low toxicity. To date, no toxic adverse events have been reported.

SDF has been used internationally for decades to arrest dental caries in primary and permanent teeth. In one study, two-thirds of all dentinal caries lesions that had progressed into the dentin were found to be arrested after treatment with SDF (Gao et al., BMC Oral Health. 16:12, 2016). When teeth with arrested dental decay are not subsequently restored with dental fillings or full coverage crowns, SDF can be re-applied every six months (Sharma et al. J Clin Diagn Res. 9:ZE08-ZE11, 2015).

SDF has clinical utility in patients, including without limitation children and adolescents, when patient cooperation for restorative dentistry is limited due to young age, situational anxiety, or intellectual and developmental disabilities. Application of SDF does not restore form and function to teeth with dental caries as do traditional restorations. However, it is an effective interim therapy when used as part of a comprehensive treatment plan.

SDF applied to dental decay or other tissues of the mouth, lips and skin causes significant, irreversible black staining due to formation of silver oxide. While superficial black staining of the skin and oral mucosa tends to resolve within days as epithelial cells slough off, unrestored caries lesions treated with SDF remain black permanently, a significant aesthetic problem especially in anterior teeth. Mechanical removal of arrested dental caries and placement of a tooth restoration do not always remove or mask the black-stained tooth structure. In addition, countertops, floors and other surfaces can become stained black if they come in contact with the silver diamine.

There is a need for compositions that are effective in arresting dental caries but that avoid the black staining associated with application of SDF.

BRIEF SUMMARY OF THE INVENTION

The present invention relates to methods and compositions for treating or preventing dental caries.

According to one aspect of the invention, compositions are provided that comprise an antimicrobial material, e.g., a silver diamine fluoride (SDF) particle, surrounded by a layer (e.g., a layer comprising $SiO_2$) that is configured to release the antimicrobial material in the presence of a environmental trigger such as a lowering pH environment. Such a composition may comprise microparticles of SDF, the microparticles comprising an outer layer of $SiO_2$. Alternative antimicrobial materials may be used as well, as described in detail below. These include, without limitation: antibiotics; antimicrobial peptides; metals, metallic compounds, and metal-containing composites; halogens; enzymes; organic cationic compounds; organic non-cationic compounds; and other non-organic compounds. Microparticles of SDF or another antimicrobial material may, for example, have an average diameter ranging from about 5 to about 40 μm, inclusive. The composition may comprise an amount of the antimicrobial material that is between about between about 1% and about 40% by weight; for example, such a composition may comprise about 38% SDF by weight, similar to current commercial compositions of non-encapsulated SDF. Such compositions may further comprise additional active and/or inactive ingredients. The compositions of the invention include, for example, varnishes, mouthwashes, chewing gum, mints, toothpastes, and adhesive strips.

According to another aspect, such a composition is configured to release the antimicrobial material in a pH-selective matter. For example, the composition optionally releases SDF at a substantially higher rate at pH 4.0 than at pH 7.0, so as to release an effective amount of SDF in the presence of an active dental caries but not (or to a substantially lesser rate) elsewhere in the mouth post-application, such as, for example, in the presence of a tooth lacking an active dental caries lesion.

According to another aspect, such a composition is configured to adhere to a surface of a tooth. Such compositions may comprise a natural adhesive, synthetic adhesive, drying adhesive, emulsion adhesive, silicone, copal, glass ionomer, cyanoacrylate, composite resin, latex, epoxy, silicone, water-based polyurethane, a denture adhesive, or any combination thereof.

According to another aspect, methods are provided for treating dental caries in an individual, such methods comprising applying an effective amount of any of the foregoing compositions to a tooth surface of the individual.

According to another aspect of the invention, methods are providing for making a composition for treating dental caries in an individual, the method comprising: providing a particle comprising an antimicrobial material, and surrounding the particle with a layer that is configured to release the antimicrobial material in the presence of a low pH environment.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

DETAILED DESCRIPTION OF THE INVENTION

1. Overview

In certain aspects, the present invention provides methods and compositions for dental care. Topical application of silver diamine fluoride (SDF) has been demonstrated to cause a substantial decrease in dental caries infection. The availability of silver ions resulting from such application is responsible for its anti-microbial activity but also leads to the formation of precipitates $AgCl$, $Ag_2O$ and $Ag_3PO_4$ that intercalate into the treated dental mineral structure and cause extreme discoloration. The present invention provides encapsulated forms of SDF that deliver SDF when required, i.e., in the presence of an active caries lesion, but sequester SDF from the oral cavity. Encapsulating SDF improves its efficacy against dental caries but also reduces cytotoxicity and discoloration.

According to one embodiment of the invention, SDF, and optionally one or more additional active and/or inactive ingredients, are encapsulated through the use of a process that involves emulsification and silica encapsulation. This encapsulation of SDF can be modified or "tuned" to regulate the amount of SDF contained in the encapsulated SDF microparticles, the diameter of the microparticles, the rate of release of SDF under various conditions, etc. Significantly, the release of SDF from such microparticles is triggered by low pH, as in the vicinity of active dental caries lesions, whereas the rest of the mouth, including unaffected teeth, exhibit a pH that is higher (closer to pH 7.4).

2. Definitions

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publications and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

The present invention relates to methods and compositions for treating or preventing caries in an individual. In particular, the present invention includes applying antimicrobial materials, including without limitation a composition comprising encapsulated silver diamine fluoride (E-SDF), to enamel and/or dentin to prevent caries, or reduce the incidence or extent of caries.

Dental caries, commonly referred to as tooth decay, is a condition in which damage to the tooth structure occurs. Dental caries is a cavity that is caused by acid release from a bacterial infection, adherent to the teeth. The tooth includes, in part, the enamel, the dentin and the pulp. The enamel comprises the outer surface of the tooth, and the dentin is the layer just below the enamel. The pulp is the central part of the tooth, which includes soft connective tissue, blood vessels and nerves. Caries, as used herein, refers to destruction or decay of the enamel, dentin and/or pulp or any combination thereof. Carious lesions refer to injury to the tooth structure that is caused by caries infection.

The presence, absence or state of caries can be determined by a health professional or lay person using methods that are known in the art. For example, early caries is determined by a visual identification of "white spot" lesions. Caries is also determined by visual and tactile exam identifying discolored or decalcified pits and fissures. Frank cavitation is identified as a clear break in the enamel. The presence of white spots, discolored or decalcified pits and fissures, or frank cavitation indicates the presence of dental caries. Inspection of visible tooth areas can be performed with a dental mirror and explorer. Caries can be identified by its texture and architecture. Healthy enamel and dentin are more dense to probing with a dental instrument, i.e., dental explorer, as compared to enamel and dentin that are infected with caries. Additionally, caries can be diagnosed with use of X-rays, especially in areas that are not easily visible. Other technologies such as fiber optic illumination, lasers and dyes can also be used to identify the presence or absence of caries.

The present invention relates to the "prevention" and/or "reduction" of caries in an individual, which is applicable to both pediatric and adult cases. Preventing caries refers to stopping active caries, delaying the onset of caries, reducing the occurrence of new caries in an individual, or reducing the number of specific oral bacteria, or changing the types of oral bacteria, or changing the relative number of bacteria. Caries can be prevented or reduced in several ways. For example, the number of teeth having caries in an individual can be reduced (e.g., the reduction in new occurrences of caries). Additionally, a reduction in the volume of caries progression can also occur. The volume of caries infection encompasses the depth of the carious lesion, the number of tooth surfaces and layers infected, and the size of the carious lesion.

As such, "reducing" caries infection or the incidence of caries refers to a decrease in one or more of the following: the number of carious lesions of the individual, the depth of the carious lesion, the tooth layers infected, and the size of the carious lesion. A patient that is subjected to the E-SDF composition of the present invention can be compared with a patient that is not subjected to the composition to determine if a reduction in caries has occurred, for use as a control. Additionally, a reduction in caries can be determined by comparing the state of caries before and after treatment. Improvement in one or more of the characteristics of caries or carious lesions indicates a reduction or treatment of caries. Additionally, the improvement of caries can be determined by a reduction in oral bacterial number, type, or relative number.

The present invention further includes treating caries. "Treating" caries refers to the cessation or reduction of progression of caries. Treating caries includes preventing the carious lesion from getting worse. For example, the carious lesion is treated when the lesion does not get larger in size and/or does not further affect additional tooth structure (e.g., penetrate from the enamel to the dentin).

Active caries refers to caries that is actively creating a lesion. Arrested caries refers to caries that has ceased its progression and is no longer creating a lesion. In an embodiment, the present invention relates to reducing the number of active caries instances in an individual treated with the E-SDF composition of the present invention, as compared to an individual that has not been treated with the E-SDF composition. In another embodiment, the present invention includes inducing or increasing arrested caries in an individual treated with a composition comprising E-SDF, as compared to an untreated individual.

As used herein, the term "antimicrobial material" means any material that, alone or in combination with other agents, kills, lyses and/or prevents the growth of microbes or otherwise reduces or eliminates the ability of a microbe to cause an oral infection or dental caries and that is suitable for dental use in compositions according to the present invention. Clinical practitioners tend to use the terms "antibiotic" and "antimicrobial" synonymously. Such antimicrobial materials include compositions that comprise one or more of the following, without limitation: antibiotics (e.g., penicillin, amoxicillin, vancomycin, clindamycin, azithromycin, clarithromycin, cephalexin, cephalosporin, cephazolin, ceftriaxone, ciproflaxin, norfloxacin, rifampin, metronidazole, nitrofurantoin, tetracycline, minocycline, streptomycin, erythromycin, gentamycin, tobramycin, sulfonamides), antimicrobial peptides (e.g., defensins such as magainin, nisin), metals, metallic compounds, and metal-containing composites (e.g., sources of silver, copper, zinc, gallium, selenium, mercury, arsenic, antimony, aluminum, bismuth, gold, lead, nickel, thallium, tin, cadmium, and cobalt ions; $TiO_2$, Cu—$TiO_2$ and $TiO_2$ nanocomposites; $Cu/SiO_2$; etc.), halogens (e.g., chlorine and iodine), enzymes (e.g., lysozyme and acylase), organic cationic compounds (e.g., quaternary ammonium compounds, chlorhexidine, octenidine, cationic surfactants [BAC, CTAB, DODAB], and chitosan), organic non-cationic compounds (e.g., furanones and triclosan), and other non-organic compounds (e.g., nitric oxide). See, e.g., Cloutier et al., Trends Biotech. 33:637-652, 2015; Mittapally et al., J. Drug Delivery and Therapeutics 8:411-419, 2018; Heidenau et al., J. Materials Sci: Materials in Medicine 16:883-888, 2005).

As used herein, the term "effective amount" means an amount of a composition comprising and antimicrobial material, e.g., E-SDF, that is effective to prevent or arrest formation of dental caries. Such a composition may also include one or more additional active ingredients, including without limitation fluoride varnish, and/or one or more inactive ingredients, as discussed below. According to one embodiment of the invention, the composition comprises 38% SDF.

"Fluoride varnish" is a highly concentrated form of fluoride that is applied to the tooth's surface as a type of topical fluoride therapy. A number of fluoride-containing varnish products are available commercially. Fluoride varnish is composed of a high concentration of fluoride as a salt or silane preparation in a fast drying, alcohol and resin-based solution. The concentration, form of fluoride, and dispensing method may vary depending on the manufacturer. While most fluoride varnishes contain 5% sodium fluoride at least one brand of fluoride varnish contains 1% difluorsilane in a polyurethane base and one brand contains 2.5% sodium fluoride that has been milled to perform similar to 5% sodium fluoride product in a shellac base.

The present invention includes methods for treating an "individual" or a "patient," and the terms are used interchangeably herein. The methods and compositions of the present invention can be used on any individual in whom caries is to be prevented or reduced. Children, between the ages of 4 years and 18 years are generally more susceptible to carious lesions, as compared to adults. The composition of teeth (enamel, dentin, and pulp) is similar for children and adults, as the adult teeth begin emerging at 6 years old, and if kept intact remain with the individual for life. Therefore E-SDF compositions are useful for treatment of adults. An embodiment of the present invention includes applying the encapsulated SDF compositions of the present invention to individuals of any age, or those having an age between about 4 and about 90 years, or about 4 and about 18 years.

Similarly, individuals with braces are more likely to get caries, or those with X-rays results showing a decrease in enamel density. Accordingly, the present invention encompasses identifying a patient that is susceptible to caries and applying the E-SDF composition of the present invention, as described herein.

Similarly, individuals that are susceptible to caries include those with salivary disorders or reduction in salivary flow or alteration in salivary contents resulting from: heritage, or Sjogrens Syndrome, or chemotherapy, or radiation therapy, or medication (e.g., for heart disease, or psychiatric disorders).

Similarly, individuals with enamel hypoplasia or *Dentinogenesis imperfecta*, or other enamel of dentinal disorders are more likely to get caries.

Process for Encapsulating Antimicrobial Materials and Other Active Ingredients

Figure 1:
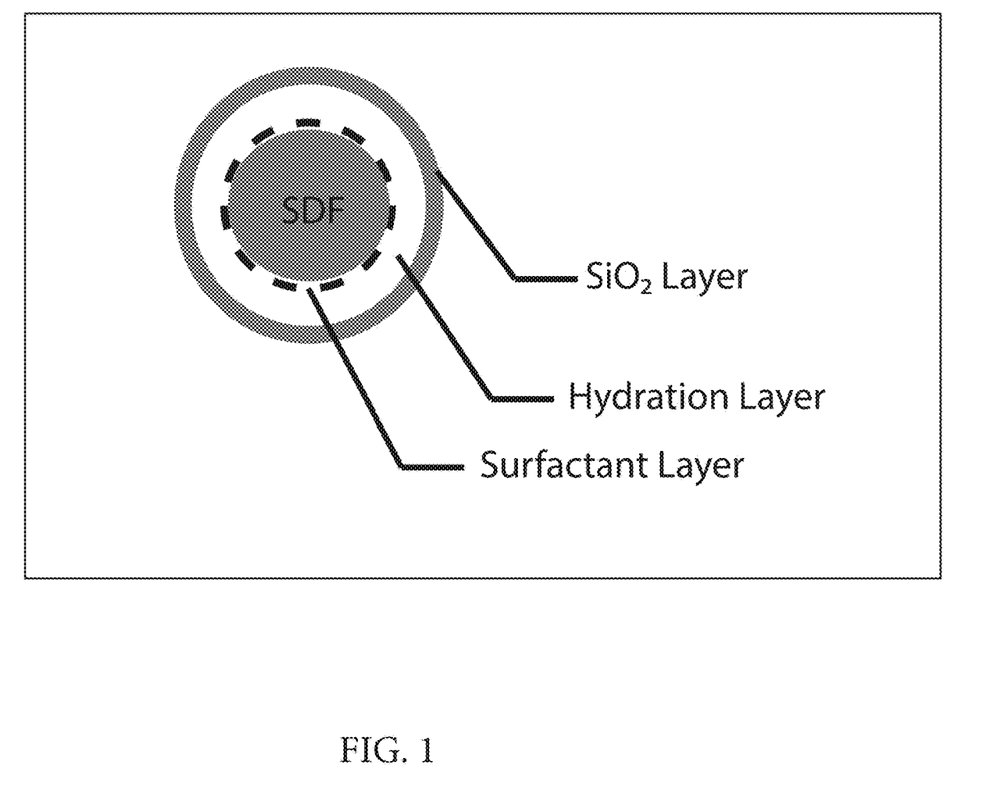
FIG. 1 shows the structure of one configuration of an encapsulated SDF (E-SDF) particle.

As discussed in Example 1 hydrophobic and hydrophilic phases are used to form emulsions. In one example, SDF in aqueous solution is added to a hydrophobic phase that includes hexadecane and a surfactant, and an emulsion is created. Tetraethyl orthosilicate (TEOS) is added to the emulsion, and encapsulated SDF (E-SDF) precipitates and is collected and dried. As shown in FIG. 1, the resulting product is an E-SDF microparticle with a multi-layer structure comprising (from the interior to exterior): (1) SDF, (2) a surfactant layer, (3) a hydration layer, and (4) an outer $SiO_2$ layer. Other antimicrobial materials may be encapsulated by a similar process.

Figure 2:
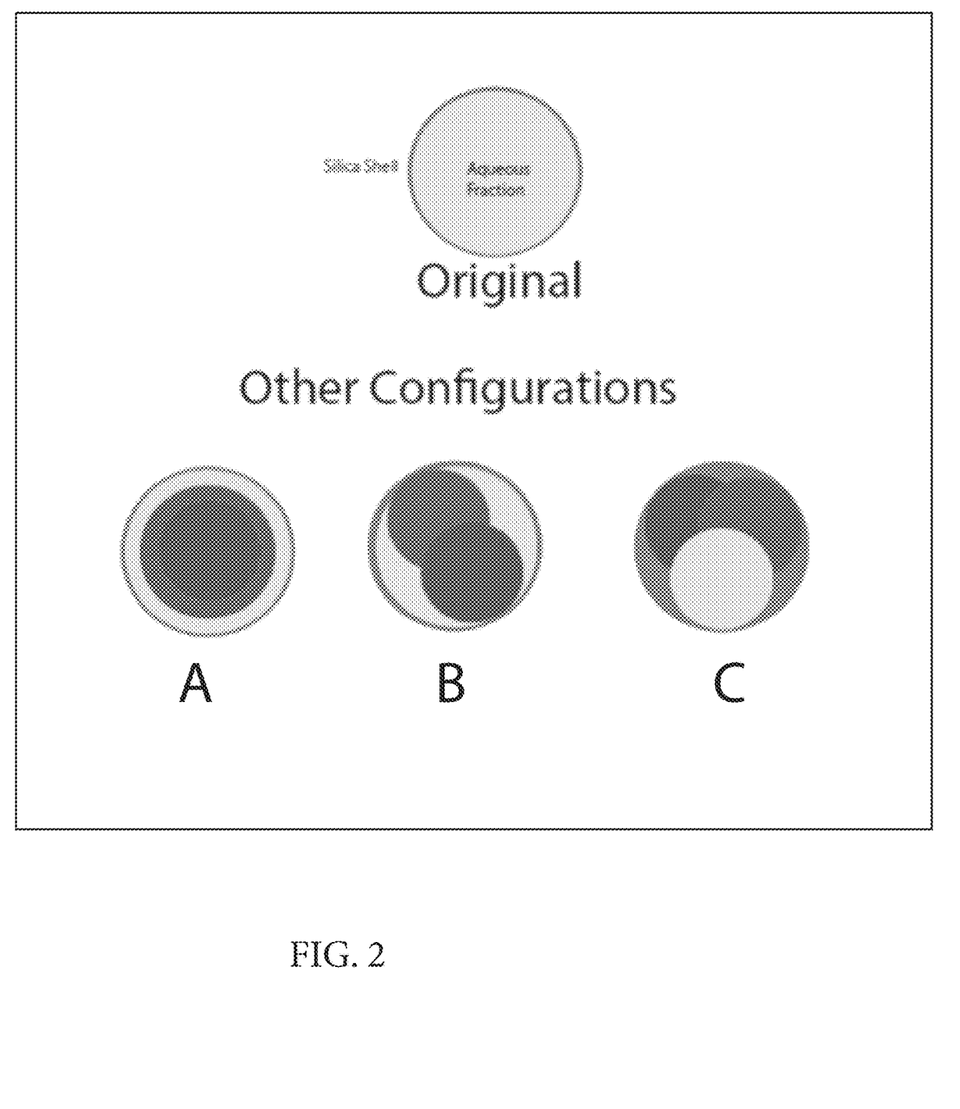
FIG. 2 shows additional configurations of E-SDF particles.

Other configurations of encapsulated SDF (or other antimicrobial materials) and other active and/or inactive ingredients, whether alone or in combination, also can be produced. Such configurations are shown in FIG. 2.

For example, a concentric or layered configuration can be achieved through a repeated process of encapsulation using alternating hydrophilic and hydrophobic phases. As shown in the diagram, the initial aqueous phase (shown as red) is formed surrounded by a hydrophobic layer (shown as green). When this initial structure is formed, it is recovered and treated with another round of encapsulation, this time with a hydrophilic layer (shown as yellow). The resulting concentric layering can continue, alternating between hydrophilic and hydrophobic layering as desired.

As another example, a multiple-emulsion configuration can be produced. In this approach two, three, four or more different aqueous solutions are combined with the hydrophobic phase to create an emulsion that includes droplets of each different solution, i.e., double, triple, or quadruple, etc. emulsions. In these ways, multiple "payloads" of active and/or inactive ingredients are loaded into the particles and the release or sequestration of a particular enzyme or molecule can be controlled temporally.

As another example, the order of the hydrophilic and hydrophobic layering can be reversed in order to produce particles with hydrophobic fractions surrounded by a hydrophilic layer and eventually encapsulated by silica.

As another example, hydrophilic phases can be encapsulated by hydrophobic layers. The initial hydrophilic phases encapsulated by hydrophobic layers are recovered and further encapsulated in a configuration with a hydrophilic inner layer and hydrophobic outer layer, and this structure can be encapsulated in silica.

In addition to the initial emulsion produced by polysiloxane in heavy, long-chain alcohols (including without limitation decanol, hexanol, or octanol), other emulsion systems can also utilize mixtures including polyethylene glycol-derived polymers (also known as polyethylene oxide or polyoxyethylene) as surfactants as well as other long-chain, soluble polymers in alcohol.

In addition to TEOS, a whole class of organosilanes/silicates can be used to create a diffusion-limited outer layer. These compounds include: trimethylpheylsilane, dimethyldiphenylsilane, bromotrimethylsilane, bromodimethylphenylsilane, dibromodimethylsilane, bromodiethylmethylsilane, tetrapropylsilicate, hexamethyldisiloxane, octamethylcyclotetrasiloxane, decamethylcyclopentasiloxane, tetramethylsilane, tetraethylsilane, chlorotrimethylsilane trichlorosilane, dichloroehtylsilane, chlorodiethylsilane, triethylsilane, and triethoxysilane.

From the initial formulation, the size, polydispersity and cohesiveness with the $SiO_2$ layer with the initial oil-water emulsion can be modified by, for example: (1) changing the surface charge of the water layer such that the interaction with the nascent $SiO_2$ layer is improved, and (2) adjusting the ionic strength of the outer water layer in the water-oil-water emulsion so that osmotic pressure drives compaction of the final $SiO_2$ layer.

The compositions of the present invention can also contain one or more additional medications or active ingredients such as antimicrobials (e.g., antifungals, antibacterials, etc.) anti-inflammatory, analgesic and immunosuppressive agents that are suitable for dental use.

Additional ingredients useful for practice of the present invention include without limitation sweeteners, flavoring and coloring agents, which could be added to achieve different tastes and flavors. Suitable sweeteners are sodium saccharine, aspartame, cyclamates, sucrose, lactose, maltose, xylitol, perillartine, AMP (aspartyl phenyl alanine methyl ester), sorbitol, mannitol, and maltitol. Suitable flavoring agents include natural and synthetic oils, e.g., spearmint, peppermint, cinnamon, clove, wintergreen, bay, citrus, lemon, lime, orange, sage, *eucalyptus*, marjoram, raspberry, menthol, and combinations thereof.

Additional materials may be incorporated in the compositions of the invention include whitening agents (e.g., urea peroxide, calcium peroxide, titanium dioxide, hydrogen peroxide, complexes of polyvinylpyrrolidone (PVP) and hydrogen peroxide), preservatives, vitamins (e.g., vitamin B6, vitamin B12, vitamin E, vitamin K), chlorophyll compounds, potassium salts (e.g., potassium nitrate) for the treatment of dental hypersensitivity, anti-tartar agents (e.g., sodium tripolyphosphate and di- and tetra-alkali metal pyrophosphate salts such as di- and tetrasodium pyrophosphate), remineralization agents such as calcium-based salts (e.g., dicalcium phosphate, tricalcium phosphate, precipitated calcium carbonate to be used alone or in combination with amino acids such as L-arginine), enzymes such as proteases to break down biofilms, or combinations thereof.

Compositions Comprising Antimicrobials (e.g., E-SDF)

Compositions of the present invention comprise an effective amount of an antimicrobial material (e.g., E-SDF) and may include other active or inactive ingredients that are compatible with oral application. Such compositions can take a number of forms, including without limitation: a varnish, rinse, toothpaste, adhesive strip, etc. In what follows, the antimicrobial is E-SDF, although any other antimicrobial, alone or in combination with E-SDF, may be used.

A composition comprising E-SDF is applied to the surface of one or more teeth in an individual. The composition includes between 1% and 40% by weight of SDF.

Varnish. According to one embodiment, such a composition includes an adhesive or gel that allows the composition to adhere to the tooth enamel for a period of between about 1 to about 10 minutes (e.g., preferably between about 2 and about 5 minutes). In another embodiment, the E-SDF composition is applied to the tooth surface for about 3 minutes. Additionally, the varnish composition also includes between 1% and 40% by weight of SDF (e.g., between 5% and 20% by weight) and a varnish carrier. Varnishes are compositions that allow one to apply the composition to one or more teeth, and the composition dries or can be cured so that the composition adheres to the teeth for a longer period of time (e.g., 5 minutes to a week to 5 years, and preferably 1 week to 1 year, 2 years, 3 years, etc.). Drying agents such as alcohol can be used. The composition can be a viscous compound that allows the composition to adhere to the tooth enamel or dentin, in another embodiment, e.g., without spreading to other oral surfaces such as the gum, lips, oral mucosa and tongue. The E-SDF compositions of the present invention, in an aspect, allows a pH-selective release of SDF to the tooth's surface during the time period for administration.

Examples of carriers that can be used include copal, denture adhesive, epoxy, silicone, latex, glass ionomer, composite resin, natural adhesives, synthetic adhesives, drying adhesives, emulsion adhesives (e.g., polyvinyl acetate) or any combination thereof, or variants thereof. The composition of the present invention can include carriers that are natural adhesives. Natural adhesives include adhesives made from inorganic mineral sources or biological sources such as vegetable matter, starch (e.g., dextrin), natural resins or from animals e.g. casein or animal glue, or bioadhesive mixtures such as gelatin and starch. Synthetic adhesives can include adhesives such as elastomers, thermoplastics, emulsion or thermosetting adhesives based on polyvinyl acetate, epoxy, polyurethane, cyanoacrylate polymers or any combination thereof. Drying adhesives can include adhesives made from a mixture of ingredients, such as polymers dissolved in a solvent. Emulsion adhesives can consist of dispersions based on polyvinyl acetate These carriers can be present in an amount that is between about 6% and about 18% by weight. The composition can further include a compound to reduce staining. Such stain reduction compounds include potassium iodide to generate silver Iodide, and/or hexafluorosilicate.

In one embodiment, the E-SDF composition of the present invention includes, for example, about 5-40% percent by weight of SDF (current commercial compositions of non-encapsulated SDF comprise about 38 percent SDF by weight, for example); up to about 10 percent by weight of glycerin; up to about 5 percent by weight of fumed silica; and an amount of varnish or adhesive additives. Examples of additives are flavorants, rosins, gums and alcohols. The composition of the present invention can also contain water.

Preferred rosins are those generally accepted for dental use, and include for example, vinsol rosin or wood rosin (e.g., as available from Hercules). The use of rosin is optional, and the amount of such rosin will vary depending upon the desired characteristics of the end product and upon the physical properties of the rosin itself.

Similarly, preferred gums include those generally accepted for dental use, and include for example, Portuguese gum (available from Calo), Arentinian gum (available from AKZO), and other gums such as Brazilian gum and the like. In a preferred embodiment of the invention, from about 50 to about 75 percent by weight (% W/V) is employed.

Additionally, alcohols for use in the composition of the present invention include those generally accepted for dental use, and include for example, ethanol. From about 20 to 35 percent by weight of ethanol can be used.

Compositions used include gels which preferably display a viscosity of 5 to 20,000 mPas, particularly preferably 100 to 5,000 mPas and quite particularly preferably 1,000 to 5,000 mPas. Viscosities can be measured using methods known in the art. In an instance, viscosities can be measured using a rotational viscometer.

The carrier of the oral composition can comprise a combination of a silicone resin and a silicone adhesive, which thus blends a strong and rigid film-forming resin with a soft elastomeric matrix adhesive. In preferred embodiments, the combination of the strong resins and soft adhesives provides an improved flexible film that is able to withstand conditions of the oral environment (e.g., temperature, moisture, pH), as well as physical agitation for an extended period of time. In various embodiments, the combination or ratios of the relative amounts of silicone resin and silicone adhesive can be adjusted to provide one or more of the following: a desired physical and chemical stability of the composition; a desired level of mucoadhesiveness related to the tackiness of the composition; a desired level of flexibility of the composition; a desired level of hardness of the composition; and control over conditions inducing disintegration of the compositions as applied to a tooth surface which further relates to a dissolution rate. For example, to achieve a desired softer consistency, an decreased level of silicone resin as compared to the adhesive will decrease the hardness and rigidity of the composition, affecting the rate of release of SDF. An increase in the level of silicone adhesive as compared to the resin will increase the tackiness level of the composition.

In another embodiment, the carrier of the oral composition can consist of a silica composition that comprises: providing an aqueous reaction medium containing an alkali metal silicate; heating the aqueous reaction medium to a temperature of from about 45° C. to about 65° C.; adding to said aqueous reaction medium an acidulating agent to form a slurry having a pH between about 5.0 to about 5.5; collecting and washing the reaction product which comprises a silica product; drying the silica product; and, optionally, milling said dried silica product.

In an embodiment, the viscosity can be set by adding a varnish former. Preferred varnish formers are cellulose-based, in particular alkyl cellulose-based, varnish formers.

In an embodiment, the carrier can be a gelling agent selected from the group consisting of hydroxyethyl cellulose, hydroxymethyl cellulose and mixtures thereof; 1.4-2.5% of colloidally dispersed silica; 5-20% of glycerol; 0.1-1% of a condensation product of ethylene oxide and polyoxypropylene glycol having a molecular weight of about 8700 and consisting of 20% weight hydrophobic polyoxypropylene glycol moiety of about 1500-1800 molecular weight and about 80% weight polyoxyethylene moiety.

A water-insoluble alkyl cellulose can be used, e.g., alkyl cellulose with a solubility of at most 0.1 g alkyl cellulose per 100 g water at room temperature. In particular, ethyl cellulose can be used.

The required quantity of varnish former depends on the type of varnish former and is preferably such that the varnish has a viscosity within the ranges given above. In the case of the alkyl cellulose preferably used as varnish former, the quantity depends on among other things its chain length and molecular weight and thus on the viscosity formed in the solution. Alkyl cellulose is preferably used in a quantity of 2 to 30 wt.-%, particularly preferably 5 to 20 weight percent (wt.-%, quite particularly preferably 6 to 12 wt.-%. A person skilled in the art can determine the quantities of other varnish formers required to set the viscosity of the encapsulated SDF-varnish composition.

Toothpaste. The compositions of the present invention further includes a toothpaste composition. The toothpaste composition includes an encapsulated SDF composition between about 0.1% and about 10% by weight (e.g., about 0.1% to about 2% by weight), and a carrier that is suitable for toothpaste. For example a toothpaste composition can include, but is not limited to, sorbital, mannitol, and/or xylitol (about 30% and 50% by weight), abrasives (about 15% to about 40% by weight), detergent (about 5% and 15% by weight). In lesser amounts, color, flavoring, glycerine, saccharin, and water are also included.

Mouthwash or rinse. The composition of the present invention further includes a mouthwash composition. The mouthwash composition includes e.g., an encapsulated SDF composition about 0.1% and about 10%, and a carrier that is suitable for a mouthwash. A mouthwash composition includes e.g., ethanol (about 10% and about 20% by weight), propylene glycol (about 5% and about 15% by weight), glycerol (about 5% and about 20% by weight). In lesser amounts, flavoring and coloring detergents can be present. A buffer and water can also be included in appropriate amounts.

A mouthwash or rinse optionally includes other ingredients such as are used in therapeutic mouthwashes or rinses. For example, an anti-plaque/anti-gingivitis agent may be used to control bacterial plaque and reduce and inhibit gingivitis, including without limitation chlorhexidine gluconate or an alcohol such as ethanol; an anti-cavity agent, including without limitation a fluoride; an anti-tartar agent, including without limitation zinc citrate; an antibacterial/antimicrobial/antibiotic agent; a chemotherapeutic agent; an enzyme, an anaesthetic, an analgesic; etc.

Adhesive strip. Additionally, the E-SDF can be incorporated into adhesive strips, as in bleaching strips, and can be applied by the patient periodically for 1-10 minutes at a time.

Methods of application. The method of the present invention includes applying the composition to the tooth surface. The method includes subjecting the tooth surface to the encapsulated SDF composition, as described herein. The SDF composition can be adhered to the tooth surface using an applicator. The applicator can be a tube applicator (e.g., such as in toothpaste or gel), tray, cotton tip, brush, and the like. The tooth surface can be prepared prior to applying the encapsulated SDF composition. The tooth surface can be cleaned, washed and/or dried to increase adherence of the encapsulated SDF composition. The encapsulated SDF composition is applied to all teeth, in the case of preventing or reducing the occurrence of caries. In another embodiment, or in addition, the encapsulated SDF composition can also be applied to teeth in the beginning stages of caries development as a treatment.

The encapsulated SDF composition in a gel carrier is applied for a period of between 1 and 10 minutes, and preferable between 2 and 5 minutes. The encapsulated SDF composition provides a concentration of SDF to the tooth surface in a sustained release fashion, or such that SDF is delivered at a concentration that does not vary by more than about 20% (e.g., not more than between about 1% and 20% variation of SDF administration).

In carrying out the methods of the present invention, the encapsulated SDF composition can be applied to an individual as a one-time treatment, or periodically. In the embodiment in which the encapsulated SDF composition is administered periodically, administration can occur e.g., daily, weekly, monthly, every 6 months, yearly, or by-yearly.

The encapsulated SDF composition in a varnish formation can be applied to the tooth surface, and the composition is cured or is allowed to dry. Once cured, SDF is released to the tooth to treat or reduce caries. The varnish composition can be applied periodically as well. The varnish composition can be applied by a dentist and cured by a curing light, as known in the art. Other varnish composition can be alcohol based and allowed to dry on the tooth surface. In this embodiment, the composition can dry or be cured to remain on one or more teeth for a longer period of time (e.g., about 5 minutes to about 5 years). In this case, the composition of the present invention provides a sustained release over a longer period of time to prevent the development of caries, or to treat carious lesions. The varnish composition can be applied every about 6 months, once 1 year, every 6 months, every 2 years, 3 years, 4 year, or 5 years.

Based on SDF's mechanism of action, bacterial genes can be targeted. As silver kills bacteria and fluoride hardens teeth, then genetic targets can be used to better target bacterial killing. It is believed that the silver and fluoride combine or precipitate to provide longer anti-bacterial and tooth hardening protection.

Although the present invention is described primarily with reference to specific embodiments, it is also envisioned that other embodiments will become apparent to those skilled in the art upon reading the present disclosure, and it is intended that such embodiments be contained within the present inventive methods.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

9. EXAMPLES

9.1 Example 1. Making Encapsulated SDF

Approximately 400 μL of 38% SDF in aqueous solution (Advantage Silver Dental Arrest LLC, Redmond, Oreg.) was added to 4 mL of 5% cetyl PEG/PPG-10/1 dimethicone (Abil® EM90; Evonik Nutrition & Care GmbH) in hexadecanol in a 15 mL polyethylene tube (Falcon) at room temperature (25° C.) wrapped in aluminum foil to prevent light exposure. The mixture was vortexed for 30 minutes, resulting in a yellow solution. The top phase (emulsion containing SDF) was collected and 2 mL was pipetted into another 15 mL polyethylene tube. An equal volume of ddH$_2$O was added and the mixture was stirred gently. 1.5X of the volume of tetraethyl orthosilicate (TEOS) was added to the emulsion and the mixture was stirred gently for 2 hours. The encapsulated SDF (E-SDF) sediments to the bottom of the tube. The E-SDF was washed with H$_2$O and 10% Tween. The product was collected and allowed to dry in a vacuum oven at 37° C. overnight.

As shown in FIG. 1, the resulting product is an E-SDF microparticle is a multi-layer structure comprising (from the interior to exterior): (1) SDF aggregate, (2) a surfactant layer, (3) a hydration layer, and (4) an outer $SiO_2$ layer.

From the initial formulation, the size, polydispersity and cohesiveness with the $SiO_2$ layer with the initial oil-water emulsion was improved in subsequent formulations. This was accomplished, for example, by: (1) changing the surface charge of the water layer (i.e., changing the pH of the surface hydration layer) such that the interaction with the nascent $SiO_2$ layer is improved, and (2) adjusting the ionic strength of the outer water layer in the water-oil-water emulsion so that osmotic pressure drives compaction of the final $SiO_2$ layer.

9.2 Example 2. Characterization of E-SDF: Optical Light Microscopy

Figure 3:
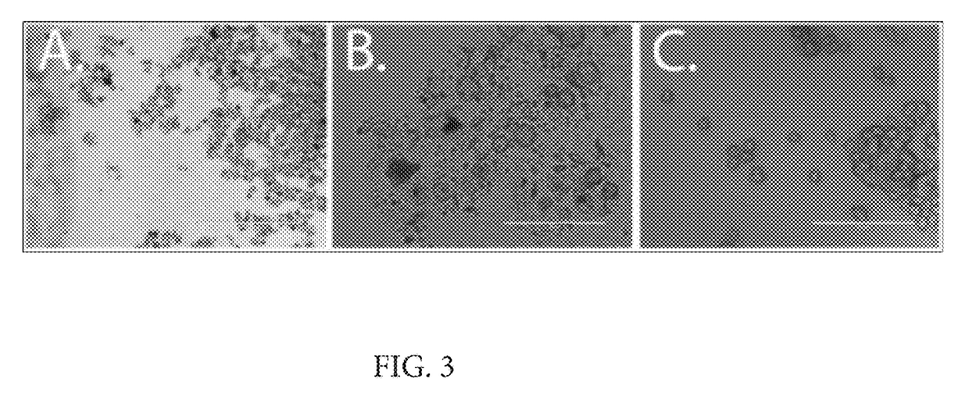
FIG. 3 shows images from optical light microscopy of E-SDF particles (A) at 2× magnification, (B) at 20× magnification, and (C) at 40× magnification.

Light microscopy was used to examine the shape, size, and morphology of E-SDF formulations. FIG. 3 shows images from optical light microscopy of E-SDF particles (A) at 2× magnification, (B) at 20× magnification, and (C) at 40× magnification. The E-SDF particles exhibit polydispersity, ranging from 10-40 μm in diameter with a majority of the particles closer to 40 μm. Optical light microscopy, provides a rapid method of assessing the degree of polydispersity and the shapes of the E-SDF particles.

9.3 Example 3. Characterization of E-SDF: Scanning Electron Microscopy

Figure 4:
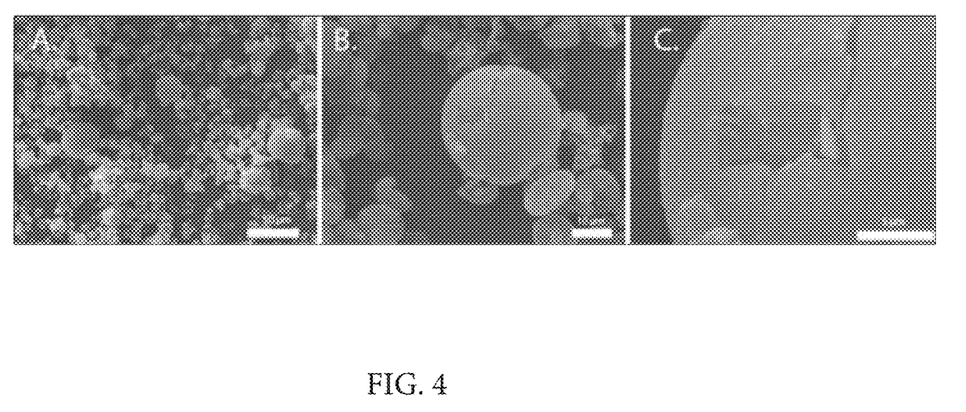
FIG. 4 shows images from scanning electron micrograph (SEM) of E-SDF particles (A) at 370× magnification, (B) at 1,600× magnification, and (C) at 6,000× magnification.

Scanning electron microscopy (SEM) was used to improve the spatial resolution to check aspects of $SiO_2$ layer formation. FIG. 4 shows images from SEM of E-SDF particles (A) at 370× magnification, (B) at 1,600× magnification, and (C) at 6,000× magnification. We imaged with 5-10 keV accelerating voltage to accomplish the spatial resolutions that are shown. SEM allows one to visualize the quality and characteristics of the outer $SiO_2$ layer in order to determine homogeneity (even layers around the particles) of the $SiO_2$ glass layer formation and surface characteristics of the final glassy layer. As shown in FIG. 4, the E-SDF particles are indeed polydispersed, but the $SiO_2$ layer is homogenous and even in every particle.

With SEM it is possible to ascertain details of E-SDF particles with up to 10 nm resolution, which enables the evaluation of final $SiO_2$ layer thickness and homogeneity as well as shape control.

9.4 Example 4. Characterization of E-SDF: Synchrotron x-Ray Micro-Computed Tomography (Synchrotron μCT)

Figure 5:
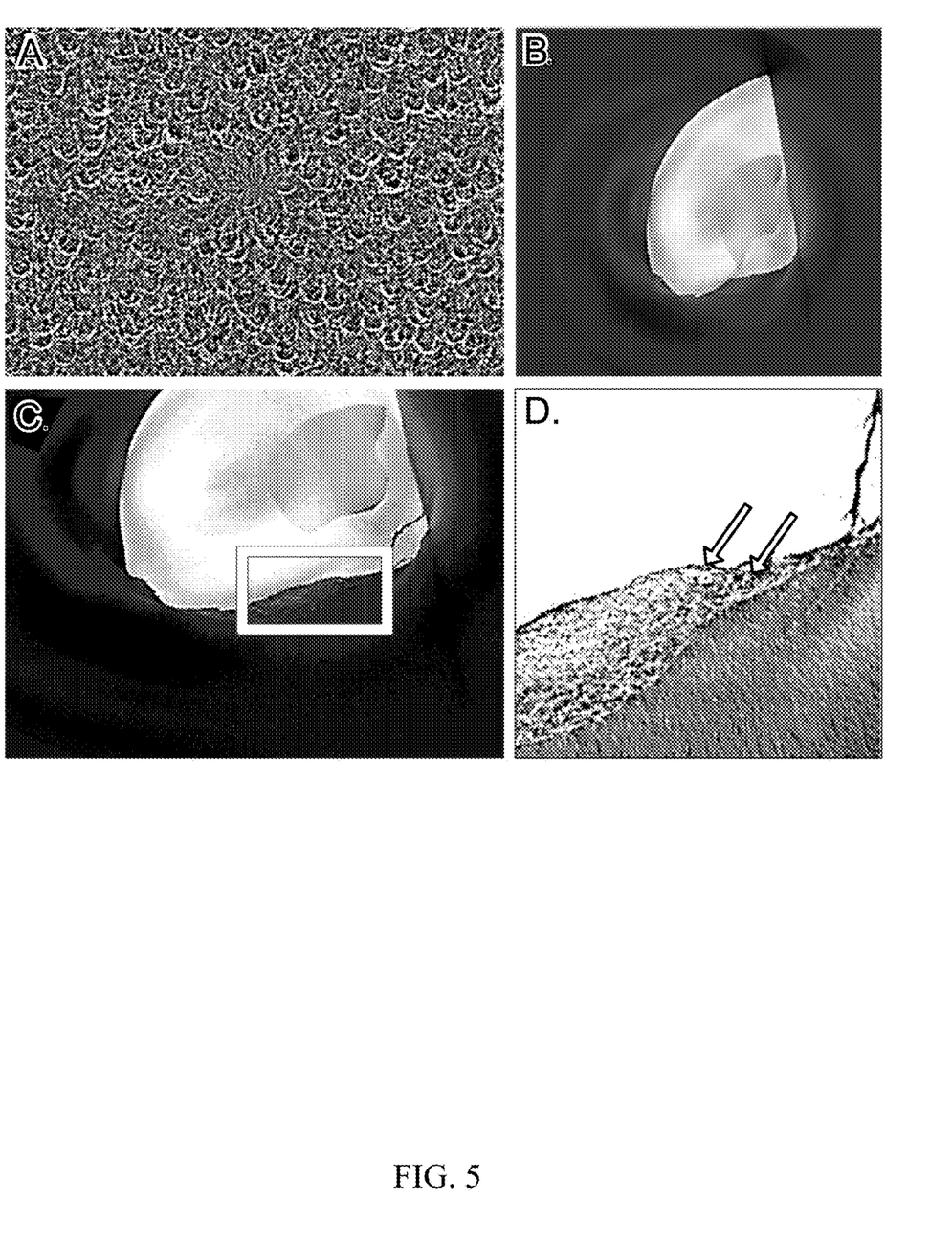
FIG. 5 shows images from synchrotron x-ray microcomputed tomography (μCT) imaging of E-SDF: (A) E-SDF particles observed alone in a dry slurry; (B) control tooth before E-SDF application; (C) tooth after E-SDF application; (D) higher magnification of E-SDF application (5×) demonstrating presence of E-SDF particles in lesion.

E-SDF was further characterized by synchrotron X-ray micro-computed tomography (synchrotron μCT) at ~20 keV energy range to visualize the "inside" of materials without mechanical agitation or sectioning. A solution of E-SDF in aqueous solution was applied directly to a cavity (dental caries), then allowed to dry at room temperature. The resulting tooth sample with E-SDF was then placed onto a sample goniometer at the Hard X-ray Tomography Beamline (BL 8.3.2, Advanced Light Source, Berkeley Labs, Berkeley, Calif.) and scanned for approximately 45 minutes. The initial scans were performed initially at 2×, then at a higher magnification, 5×. Images from synchrotron x-ray micro-computed tomography (μCT) imaging of E-SDF are shown in FIG. 5: (A) E-SDF particles observed alone in a dry slurry; (B) control tooth before E-SDF application; (C) tooth after E-SDF application; (D) higher magnification of E-SDF application (5×) demonstrating presence of E-SDF particles in lesion.

Table 1 shows measurements of individual E-SDF particles by Synchrotron μCT. By measuring the parameters of typical particles, the average size and $SiO_2$ thickness can be determined.

The use of synchrotron μCT allows one view E-SDF particles with sub-micron resolution without mechanical manipulation and hence avoiding sample preparation artefacts such as cracks and indentations.

TABLE 1

Measurements of diameter and $SiO_2$ E-SDF particles by synchrotron μCT.

| E-SDF Particle | Diameter (μm) | $SiO_2$ Layer Thickness (μm) |
|---|---|---|
| N1 | 41.2 | 7.9 |
| N2 | 39.0 | 3.9 |
| N3 | 45.2 | 5.5 |
| N4 | 42.6 | 4.4 |
| N5 | 42.3 | 6.4 |
| Average Parameters | 42.1 ± 4.5 | 5.2 ± 3.5 |

9.5 Example 5. Characterization of E-SDF: Inductively-Coupled Plasma—Optical Emission Spectroscopy (ICP-OES)

Through use of ICP-OES, one can measure the absolute amount of silver (to 0.001 μg/mL) found in a volume of E-SDF particles and compared those amounts to typical clinical SDF treatments. This method is especially useful to optimize the amounts to be delivered in the various formulation utilized for the encapsulation.

The results of ICP-OES on E-SDF particles produced the results shown in Tables 2 and 3 below.

TABLE 2

ICP-OES of different stages of the E-SDF process

| Sample | ICP-OES (μg/mL, n = 3) |
|---|---|
| 1: Initial oil-water emulsion | 4507.8 ± 253.9 |
| 2: Hydration layer stage | 784.1 ± 72.88 |
| 3: Initial addition of TEOS | 1188.1 ± 250.8 |
| 4: After incubation with TEOS | 784.5 ± 56.44 |

TABLE 3

ICP-OES measurements of the E-SDF encapsulation process from initial emulsion to final E-SDF particles: the various stages of the encapsulation process and the related amounts of detectable silver. (Also included as a reference is an ICP-OES measurement of a standard SDF application as a control for comparison purposes.)

| Sample | ICP-OES (μg/mL, n = 3) |
|---|---|
| Initial oil-water emulsion | 65.85 ± 2.18 |
| Initial water-oil-water emulsion | 1194.7 ± 62.1 |
| Initial addition of TEOS | 1222.05 ± 328.5 |
| Defined $SiO_2$ layer encapsulating SDF | 226.7 ± 47.7 |
| Standard SDF application | 16,552.5 ± 251.5 |

ICP-OES is a sensitive method for direct measurement of the amount of silver in solution. Of interest is the comparison of silver from E-SDF and normal clinical SDF treatment. As shown in Table 2, a volume of E-SDF particles resuspended in ddH2O is found to be approximately 226.7 µg/mL, whereas in a similar volume of clinical SDF sample, the silver content is found to be 16.6 mg/mL, approximately a 70× difference in silver concentration. This further supports the idea that physical properties can be altered by varying concentration, specifically in this case the coloration from silver precipitation.

Additionally, since we can evaluate the approximate size of the E-SDF particles and as a result, we can also determine the internal volumes of the E-SDF. It is possible to determine approximately how much silver is found in an individual E-SDF particle by assuming: (1) hexagonal close packing of the E-SDF particles, and (2) an average diameter of 40 µm for E-SDF particles. Maximum hexagonal packing density will be $\pi/3\sqrt{2} \approx 0.740$. From a 10 µL volume, ICP-OES results in measurement of a concentration of 226.7 µg/mL (Table 2), from which it can be inferred that approximately 441.7 particles of E-SDF particle are present. Thus, each E-SDF particle has a volume of approximately 1.68 nL of SDF.

9.6 Example 6. Characterization of E-SDF: UV Spectrophotometry

Ultraviolet (UV) light absorption of silver in aqueous solution occurs at 400 nm. Table 4 shows the amount of silver detected by UV spectrophotometry at various steps in the encapsulation process.

TABLE 4

| UV Spectrophotometry at 400 nm at various stages of E-SDF formation | |
|---|---|
| Step | UV Absorption (a.u., n = 3) |
| Initial SDS oil-water emulsion | >3.0 |
| Initial TEOS addition to SDF emulsion | 1.95 ± 0.05 |
| Defined SiO$_2$ layer encapsulating SDF | 1.75 ± 0.01 |

By layering the E-SDF with an increasingly opaque material (siloxane, water, and SiO$_2$), the silver is obscured. The ability to measure reliably and accurately the relative amounts of silver from E-SDF release enables validation of the effectiveness and efficacy of E-SDF for clinical use.

9.7 Example 7. Characterization of E-SDF: pH Reactivity

By determining the relative release of silver from E-SDF as a function of pH, it is possible to optimize the parameters (e.g., SiO$_2$ layer thickness and particle size) to improve effective release of SDF at clinically relevant pH ranges. UV spectrophotometry (at 400 nm) was used to determine the release of silver from 100 mg of E-SDF was performed over a range of pH from 4.0-9.0.

TABLE 5

| Determining Relative Amounts of Silver Released Into Solution From E-SDF Particles as a Function of pH. | |
|---|---|
| pH | Absorption (a.u., n = 3) |
| 9.0 | 0.252 ± 0.363 |
| 7.0 | 0.464 ± 0.164 |
| 6.0 | 0.632 ± 0.279 |
| 4.0 | >3.0 |

The pH reactivity is a important factor in assessing the release of SDF from E-SDF particles. SDF release is indeed detectable at low pH, specifically at pH 4 and below. The relative amounts of SDF detectable at higher pH can be attributed to artefacts (cracked or opened E-SDF particles) or residual SDF not fully encapsulated during the E-SDF bulk process, which can be seen by the progressive trend of less available SDF at higher pH levels.

9.8 Example 8. Comparison of SDF and E-SDF

Figure 6:
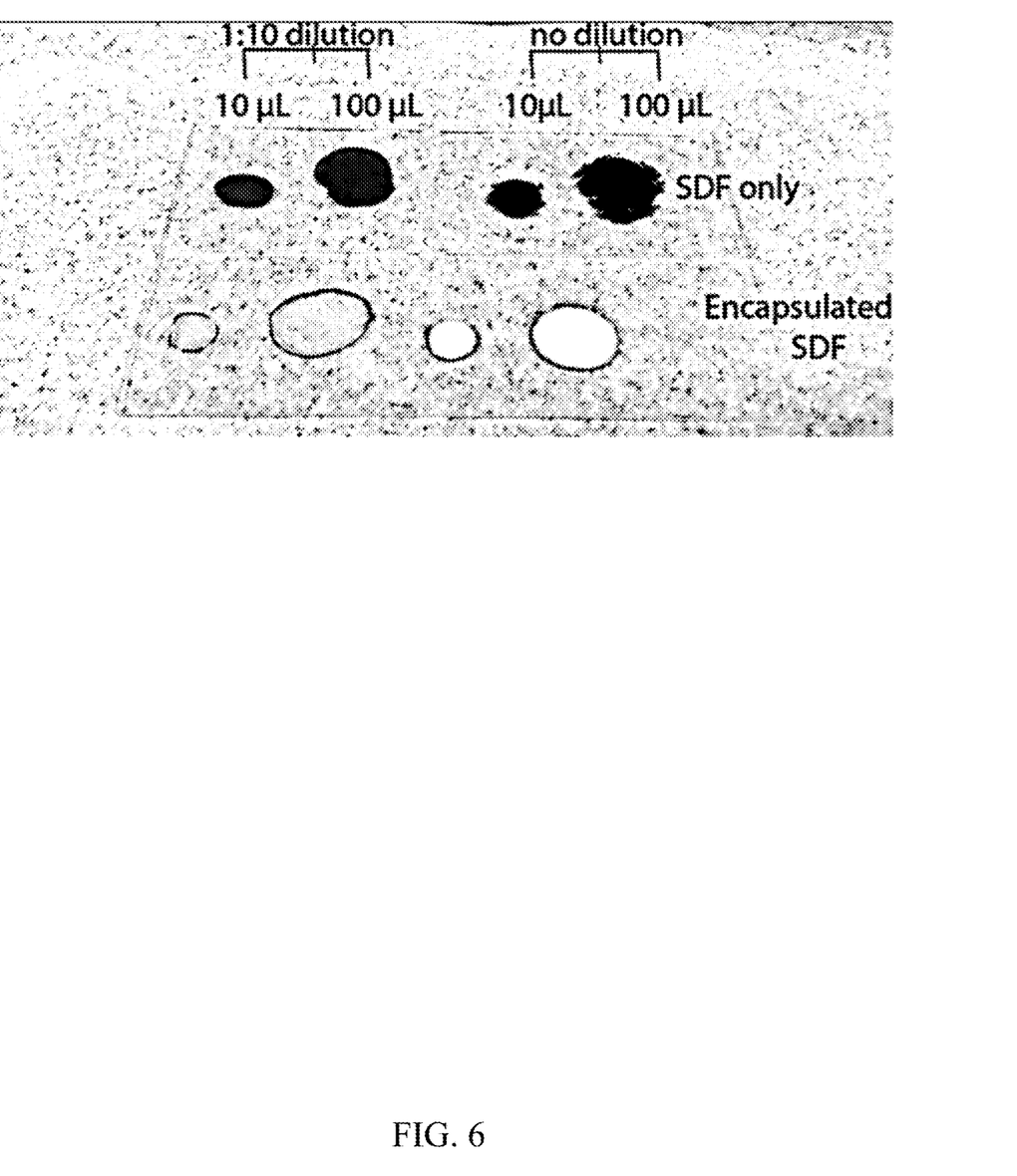
FIG. 6 shows the results of application of 10 μL and 100 μL SDF (unencapsulated) and encapsulated SDF at 1:10 dilution and undiluted. Top row: SDF. Bottom row: encapsulated SDF.

FIG. 6 shows the results of application of SDF versus E-SDF. In the top row, 10 µL and 100 µL of SDF (unencapsulated) at 1:10 dilution and undiluted were applied to glass objective slides. In the bottom row, similar quantities and dilutions of E-SDF were applied. The E-SDF displays dramatically different staining of the glass substrate, which is observable by visual inspection.

By encapsulating SDF, the release of SDF can be regulated, and the amounts of SDF exposure can also be limited. Specifically, by encapsulating the SDF, the amount of SDF applied to the caries lesion can be regulated such that none of the typical black staining occurs. We demonstrate here that E-SDF particles can reduce the amount of silver applied but retain function without discoloration. The effects of encapsulation on discoloration are obvious. E-SDF retains effectiveness in killing dental caries bacteria and reducing or eliminating formation of dental caries as demonstrated by its effect on the growth of S. mutans in microbiological assays.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method for treating dental caries in an individual, the method comprising applying an effective amount of a composition to a tooth surface of the individual, said composition comprising microparticles comprising an antimicrobial material, a surfactant layer, and a hydration layer that are surrounded by an SiO$_2$ layer that is configured to release the antimicrobial material in the presence of a tooth having an active dental caries lesion but to not release the effective amount of antimicrobial material in the presence of a tooth lacking an active dental caries lesion.

2. The method of claim 1, wherein the antimicrobial material comprises silver diamine fluoride (SDF).

3. The method of claim 1, wherein the microparticles have an average diameter of 5 to 40 µm.

4. The method of claim 1, further comprising an additional active ingredient.

5. The method of claim 1, further comprising an inactive ingredient.

6. The method of claim 1, wherein said composition is selected from the group consisting of a varnish, a mouthwash, a toothpaste, and an adhesive strip.

7. The method of claim 1, comprising an amount of the antimicrobial material between about between about 1% and about 40% by weight.

8. The method of claim 1, wherein said composition is configured to adhere to a surface of a tooth.

9. The method of claim 8, comprising a member of the group consisting of a natural adhesive, a synthetic adhesive, a drying adhesive, an emulsion adhesive, silicone, copal, glass ionomer, cyanoacrylate, composite resin, latex, epoxy, water-based polyurethane, a denture adhesive, or any combination thereof.

10. The method of claim 1, wherein the antimicrobial material is in a solution and is selected from the group consisting of silver diamine fluoride, penicillin, amoxicillin, vancomycin, clindamycin, azithromycin, clarithromycin, cephalexin, cephalosporin, cephazolin, ceftriaxone, ciproflaxin, norfloxacin, rifampin, metronidazole, nitrofurantoin, tetracycline, minocycline, streptomycin, erythromycin, gentamycin, tobramycin, sulfonamides, defensin peptides, gallium compound, selenium compound, mercury compound, arsenic compound, antimony compound, bismuth compound, lead compound, nickel compound, thallium compound, tin compound, cadmium compound, cobalt compound, lysozyme, acylase, octenidine, benzalkonium chloride, cetyltrimethylammonium bromide, Dimethyldioctadecylammonium bromide, and furanone.

* * * * *

UNITED STATES PATENT AND TRADEMARK OFFICE
CERTIFICATE OF CORRECTION

| | | |
|---|---|---|
| PATENT NO. | : 11,642,371 B2 | Page 1 of 1 |
| APPLICATION NO. | : 17/108947 | |
| DATED | : May 9, 2023 | |
| INVENTOR(S) | : Seto et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 37 days.

Signed and Sealed this
Thirty-first Day of December, 2024

Derrick Brent
*Acting Director of the United States Patent and Trademark Office*